United States Patent [19]  [11] 4,066,510
Thilly  [45] Jan. 3, 1978

[54] ASSAY FOR MUTAGENESIS IN DIPLOID HUMAN LYMPHOBLASTS

[75] Inventor: William G. Thilly, Cambridge, Mass.

[73] Assignee: Massachusetts Institute of Technology, Cambridge, Mass.

[21] Appl. No.: 689,432

[22] Filed: May 24, 1976

[51] Int. Cl.$^2$ ............................................. C12K 1/00
[52] U.S. Cl. .............................................. 195/103.5 R
[58] Field of Search ................................... 195/103.5 R

[56] References Cited
PUBLICATIONS

Rothblat et al., Growth, Nutrition and Metabolism of Cells in Culture, pp. 238, 239 and 329, vol. 1, (1972).

Primary Examiner—Alvin E. Tanenholtz
Attorney, Agent, or Firm—Arthur A. Smith, Jr.; Robert Shaw; David E. Brook

[57] ABSTRACT

An assay is disclosed for determining mutagenic damage caused by the administration of a known or suspected mutagen to diploid human lymphoblastoid cell lines. After administration of or exposure to a mutagenic agent, the lymphoblasts are incubated for a sufficient number of generations to allow full expression of phenotypic resistance to 6-thioguanine or other purines which serve as substrates for hypoxanthine guanine phosphoribosyl transferase (HGPRT). A surprising discovery is the remarkably long length of time required for such phenotypic expression. After the phenotypic lag has passed, the mutant fraction can be determined to complete the assay. A nontoxic, active, sterile microsomal drug-metabolizing system compatible with mammalian cell bioassays is also disclosed which can be used in the assay to determine metabolite-caused mutagenesis. These bioassay systems can be used by genetic toxicologists to determine the potential genetic hazards to human beings for a variety of suspected or known mutagens, including newly developed chemicals.

10 Claims, 11 Drawing Figures

ASSAY FOR MUTAGENESIS IN DIPLOID HUMAN LYMPHOBLASTS

GOVERNMENT SPONSORSHIP

Work relating to this invention was partially supported by grants from the National Institutes of Health. Specifically, these grants were NCI 5-RO1 CA 15010-02 ET from the National Cancer Institute and NIEHS 5-PO1 ES 00597 from the National Institute of Environmental Sciences.

BACKGROUND OF THE INVENTION

1. Field of the Invention

This invention is in the field of biochemistry and specifically relates to genetic toxicology.

2. Description of the Prior Art

The use of lower organisms to evaluate the genetic effects of chemical and physical agents began in the studies of mustard gas effects on Drosophilia during World War II, and rapidly progressed with the use of prokaryotes and neurospora. However, work with mammalian cells was hindered by lack of technical development until Puck and Marcus provided a cloning technique for the HeLa human cell line. Puck, T.T. and Marcus, P. I., *Proc. Nat. Acad. Sci.*, 41, 432-437 (1955).

Szybalski and Syzbalska developed a forward and backward selective system for detecting mutants negative or positive for the activity of x-linked hypoxanthine guanine phosphoribosyl transferase (HGPRT) in a heteropoloid human line, D98. Szybalski, W. and Szybalska, E. H., "Drug Sensitivity as a Genetic Marker for Human Cell Lines," *Univ. Mich. Med. Bull.*, 28, 277-93 (1962). However, they observed no mutagenic effects when this line was treated with a series of physical and chemical agents known to be effective mutagens in other biosystems. Szybalski, W., *Cold Spring Harbor Symposium on Quantitative Biology*, 29, 151-159 (1964).

Later work with mammalian cell mutagenesis centered on the use of two near-diploid hamster lines (CHO) and V79, for which the dose-dependent mutagenic effects of ultraviolet and ionizing radiation were studied, as well as a series of chemicals. Kao, F. T. and Puck, T. T., "Genetics of Somatic Mammalian Cells." IX. Quantitation of Mutagenesis by Physical and Chemical Agents, *J. Cell Physiol.*, 74, 245-257 (1969); Chu, E. H. Y., P. Brimer, K. B., Jacobsen and E. V. Merriam, "Mammalian Cell Genetics. I. Selection and Characterization of Mutations Auxotrophic for L-glutamine or Resistant to 8-azaguanine in Chinese Hamster Cells in Vitro," *Genetics*, 62, 359-377 (1969); Arlett, C. F. and J. Potter, "Mutation to 8-azaguanine Resistance Induced by γ-irradiation in a Chinese Hamster Cell Line," *Mutation Res.*, 13, 59-65 (1971); Bridges, B. A. and J. Huckel, "Mutagenesis of Cultures Mammalian Cells by X-irradiation and Ultraviolet Light," *Mutation Res.*, 10, 141-151 (1970).

More recent studies have attempted to extend the mutagenesis protocols originally established for cell lines of rodent origin to those of human origin. Albertini, R. J., and Demars, R., "Detection and Quantification of X-ray-induced Mutation in Cultured, Diploid Human Fibroblasts," *Mutat. Res.*, 18, 199-244 (1973); Maher, V. M. and Wessel, J. E., "Mutations to Azaguanine Resistance Induced in Cultured Diploid Human Fibroblasts by the Carcinogen N-acetoxy-2-acetylaminofluorene," *Mutat. Res.*, 28, 277-284 (1975). Researchers have noticed marked differences between human and rodent cells in their ability to repair chemically induced damage to DNA, and variations may be expected among other species. Buhl, S. N. and Regan, J. D., *J. Biophys.*, 14, 519-527 (1974); and Rauth, A. M., Tammemagi, M., and Hunter, G., *J. Biophys.*, 14, 209-220 (1974). Because of these differences, the use of human cells may prove necessary, and is certainly desirable, in obtaining relevant data for predicting the hazard that a particular chemical or other suspected mutagen poses for human beings.

One serious problem with most present protocols for performing mammalian cell mutation assays, however, is that the observed mutant fraction varies as a function of time after treatment with a selective agent. This finding is well documented for the appearance of 6-thioguanine (6TG) or 8-azaguanine (8AG)-resistant mutants in various rodent fibroblast systems and in human fibroblasts. Chu, E. H. Y. and Malling, H. V., *Proc. Natl. Acad. Sci. U.S.A.*, 61, 1306-1312 (1968); Bridges, B. A. and Huckle, J., *Mutat. Res.*, 10, 141-151 (1970); Arlett, C. F. and Harcourt, S. A., *Mutat. Res.*, 14, 431-437 (1972); Maher, V. M. and Wessel, J. E., *Mutat. Res.*, 28, 277-284 (1975). Recently, similar instability of a mutant fraction resistant to ouabain was reported for a Chinese hamster fibroblast line after methylnitronitrosoguanidine (MNNG) treatment. Davies, P. J. and Parry, J., *Genet. Res.*, 24, 311-314 (1974). Such findings are, of course, inconsistent with the expected bahavior of stable hereditary changes.

One researcher has reported maintaining a mutagen-treated mouse cell population in near exponential growth for 2 weeks by frequent passaging to fresh plates. By adding a selective agent, 6-thioguanine, to the plates at various times after mutagen treatment and then measuring the fraction of recovered mutants, he has shown that the mutant fraction increases over a period of 8-10 days, finally reaching a stable maximum. Chasin, L., "The Effect of Ploidy on Chemical Mutagenesis in Cultured Chinese Hamster Cells," *J. Cell Physiol.*, 82, 299-308 (1973). A second laboratory has reported confirmation of this finding with anchorage-dependent cells. Hsie, A. W., Brimer, P. A., Mitchell, T. J. and Goslee, D. G., "The Dose-response Relationship for Ethyl Methane Sulfonate-induced Mutations at the Hypoxanthine-guanine Phosphoribosyl Transferase Locus in Chinese Hamster Ovary Cells," *Somatic Cell Genetics*, 1, 247-261 (1975).

Additionally, some researchers have recently added mutagens to human lymphoblasts, but they failed to measure resulting mutagenesis in a quantitative way. Sato, K., Slesinski, R. S. and Littlefield, J. W., *Proc. Natl. Acad. Sci. U.S.A.*, 69, 1244-1248 (1972).

SUMMARY OF THE INVENTION

This invention is based upon the discovery that a surprisingly long period of time is required for full expression of mutagenesis in diploid human lymphoblastoid cell lines. This period of time is referred to herein as the "phenotypic lag." When this phenotypic lag is properly taken into account, diploid human lymphoblast systems have been found to behave in the manner expected or true genetic mutation.

More specifically, it has been shown that the administration of mutagens, such as known mutagenic chemicals or ultraviolet light, to human lymphoblasts results in mutagenic damage at the hypoxanthine guanine phosphoribosyl transferase (HGPRT) locus. This mutagenic damage can be quantitatively determined based upon the resistance of treated lymphoblasts to purines which serve as substrates for HGPRT. 6-thioguanine (6TQ) is one such purine, and this compound is toxic to most mammalian cells, including nonmutant lymphoblasts. The exceptions are rare variants lacking either normal HGPRT activity or the ability to transport such purine analogs.

The assay protocol for determining potential mutagenesis in humans is based upon the discovery of the remarkably long phenotypic lag required for expression of cell resistance to suitable purines after administration of a mutagen. In this protocol, human lymphoblastoid cell lines are first cultured and then exposed to the suspected mutagen to be tested. After exposure, the treated cells are resuspended in fresh medium and incubated for a sufficient number of generations to allow them to express their full phenotypically-developed resistance to 6TG or other purine. When such resistance has reached a constant value, the degree of mutagenesis can be determined by calculating the mutant fraction or by other techniques. By administering different dosages of the suspected mutagen, dose-response relationships can be established.

Metabolizing systems can also be added to the lymphoblast cultures to determine whether any metabolite by-products of a tested compound are mutagens. A particularly effective, non-toxic, active, sterile microsomal drug metabolizing system has been developed for use in mutagenesis assays, including that described herein. Standard microsomal or post-mitochondrial supernatant metabolizing preparations are improved by filter sterilization, limited time of incubation and addition of nicotinamide adenine dinucleotide, reduced form (NADH).

The assay procedure described herein has many advantages over those previously known. The use of an established line of diploid human lymphoblasts, for example, permits the continuous growth of treated suspension cultures which obviates the physical manipulations (passageing) needed to maintain growth of anchorage-dependent cell lines. Since it is known that many mutagens are specific to certain species, a most significant advantage of this assay procedure is that it specifically employs human diploid lymphoblasts, rather than lower mammalian cells.

DESCRIPTION OF PREFERRED EMBODIMENTS

Figure 1:
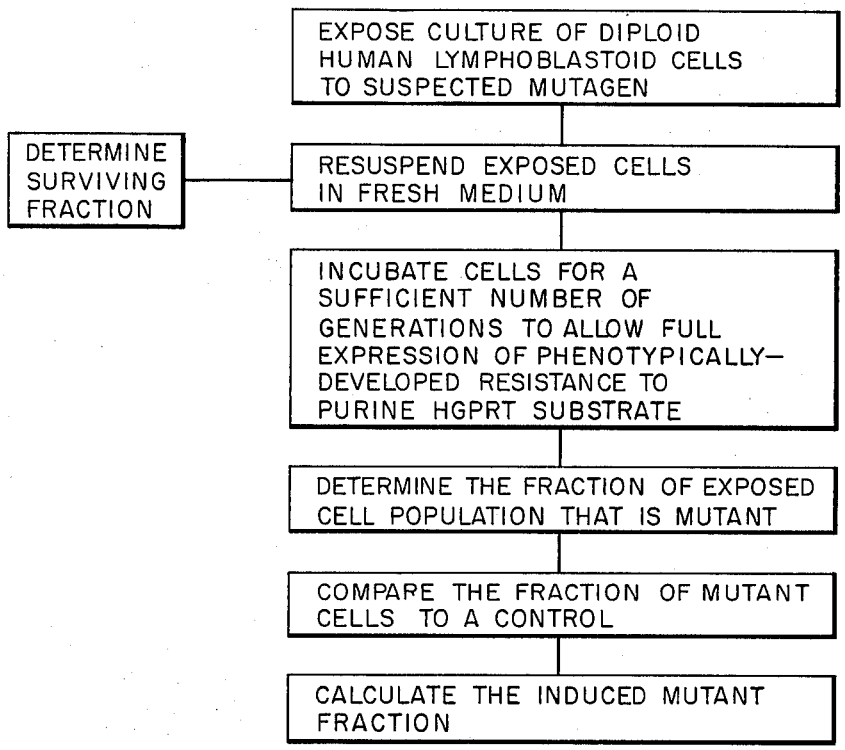
FIG. 1 is a flow diagram illustrating the mutagenesis assay protocol described herein.

Referring now to FIG. 1 in more detail, it can be seen that the first step in the mutagenesis assay is the exposing of a culture of human diploid lymphoblastoid cells to a suspected or known mutagen. For example, in the case of chemical mutagents, these can simply be added to the culture suspension. Physical agents, such as electromagnetic or nuclear radiation, can also be used. For example, a culture of growing diploid human lymphoblasts can be irradiated with ultraviolet light to test for mutagenesis. Other conditions, such as heat, cold, or exposure to other microorganisms, such as viruses, can also be used to cause mutagenesis. It is desirable to establish exponential cell growth prior to mutagen exposure. The dosage of mutagen, exposure time, etc., can vary widely. It is believed that any dosage and/or exposure can be used as long as some fraction of the treated cells survive. To check this, the cells are resuspended after exposure to the mutagen in fresh medium and the surviving fraction is determined by plating. In cases where the mutagen being tested is exceptionally cytotoxic, it is necessary to use more cells initially. In a typical assay, the cells are exposed to a suspected chemical mutagen for about 24 hours, but there is nothing critical about this time and wide variations are possible.

After treatment, there is a period before cell growth and division provides a sufficient number of live cells to allow the determination of mutant fraction. This is known as the "growback" period. In the work described herein, it has been noted that this period varies significantly for different mutagens studied. It may also vary with dosage, particular cell line employed, culture conditions, etc. Generally, the required growback period has not been utilized in assay procedures for mammalian cell mutagenesis heretofore known. This may be because most past assays employed anchorage-dependent mammalian cells which were grown on Petri dishes. Such dishes are typically limited to an initial inoculation of approximately $5 \times 10^4$ cells/dish. However, the use of lymphoblast cells, which grow unattached as suspended particles in suspension, permits the facile exposure of up to $10^8$ or more human cells simultaneously in an environment which permits continued growth and division after treatment.

The degree of mutagenesis caused by exposure to the mutagen is related to the expression of resistance to a purine HGPRT substrate, such as 6TG, in the growing treated cells. It is known that 6TG kills cells containing active HGPRT. Cells capable of forming clones in the presence of 6TG have lost, via mutation, the ability to synthesize active HGPRT.

It has been surprisingly found, however, that the period required for full phenotypic expression of 6TG resistance is much longer than previously recognized.

For example, human diploid lymphoblast cells (MIT-2) have been found to have a phenotypic lag of between 6 and 12 days when they are treated with known chemical mutagens, such as ethyl methane sulfonate, methylnitrosourea, methylnitronitrosoguanidine, bromodeoxyuridine, and ICR-191.

The biochemical basis for this extremely long phenotypic lag is not fully understood. It could be related to the intracellular degradation of HGPRT protein or mRNA or simply to the time required to dilute the amount of active HGPRT contained in the cells prior to mutation. The celleular HGPRT content at the time of mutation, the rate of HGPRT degradation, the rate of cell division, the efficiency of a particular species HGPRT in forming a toxic product from the tested mutagen, and the sensitivity of the specific cell type used to the toxic product probably all influence the period of phenotypic lag.

After the required period of time for full phenotypic expression of cell resistance has passed, the induced mutant fraction can be determined. This is determined by first determining the fraction of the exposed cell population that is mutant; comparing that fraction of mutant cells to a control; and then calculating the induced mutant fraction from these. Thus, the induced mutant fraction is equal to the ratio of cell cloning efficiency in the presence of the purine HGPRT substrate to the cloning efficiency in its absence. It has been found that the induced mutant fraction is stable after sufficient time has been allowed for full phenotypic expression of cell resistance for human diploid lymphoblastoid cells treated with known mutagenic agents. This is, of course, characteristic of true mutagenic cell damage.

The cell line used in most of the actual experimental work described herein is a line of human lymphoblasts which is a clonal derivative of the PGLC-33 line originally isolated from a young female with mononucleosis. This line is designated MIT-2. It has been grown in suspension cultures in a continuous phase (doubling time, 16.8 hours) by daily dilution with RPMI 1640 medium, without antibiotic, but supplemented to 10% with fetal calf serum. Other diploid or near-diploid human lymphoblastoid cell lines or diploid human cell lines capable of continuous division in suspension culture are also suitable for use in these assays. The ploidy requirement is for one and only one active X-chromosome which carries the gene for HGPRT. Specific examples of suitable cell lines are those designated by the American Type Culture Collection as CCRF-CEM, CCRF-SB, CCRF-HSB-2 and EB-3. Standard incubation and culturing techniques, as well as standard culture media, with or without supplements, can be used with such cell lines. Those skilled in the art will be able to ascertain, with no more than routine experimentation, other suitable cell lines and the preferred growth conditions for any particular line.

Although the experimental work described herein was performed using 6-thioguanine, other purines which act as HGPRT substrates are also suitable. Specific additional examples are 8-azaguanine and 8-azahypoxanthine. Those skilled in the art will also know or be able to ascertain using no more than routine experimentation, other suitable purine HGPRT substrates.

It is often desirable to add an active drugmetabolizing system to mutagenesis assay systems to help in interpreting negative results. This is because the enzyme systems represented by the cell microsomes often catalyze chemical reactions producing genetically active derivatives from inactive precursors. In assays such as that described herein, the lymphoblast cells grow rapidly in culture and do not express significant drug metabolizing activity. The addition of an active drug-metabolizing system to these cell cultures, therefore, makes a more complete bioassay system.

One known metabolizing system is formed from a dilute liver post-mitochondrial supernatant (PMS) obtained from rats previously treated with phenobarbital or methylcholanthrene. Ames, B. N., *Mutagenic Effects of Environmental Contaminants,* eds. Sutton, H. E. and Harris, M. I., 57–66, Academic Press, N. Y. (1972). Those skilled in the art will know or be able to ascertain others, using no more than routine experimentation.

An active, drug-metabolizing system particularly suitable for use in the mutagenesis assays described herein, or in other bioassays, can be prepared as follows. In the first step, mammalian tissue, such as rat liver tissue, is homogenized in an aqueous suspension medium. Relatively large cellular particles are removed to produce a post-mitrochondrial supernatant (PMS). The PMS supernatant is usually not free of contamination, but this can be removed by filtering the PMS through a filter having an appropriate pore size.

There are many possible suitable sources of mammalian tissue, with rat liver being one which is commonly used. For assays of human mutagenesis potential, it is preferred, of course, to use active human tissue enzymes such as might be obtained from human liver tissue. Homogenization can be performed by any of the known techniques usually employing homogenizers which are designed for just this purpose. The relatively large particles, or mitochondria, can be removed by centrifuging the homogenized material to produce a supernatant fraction of PMS. This serves as a source of microsomal enzyme. After removal of the mitochondria, the supernatant is filtered through filters having a port size sufficient to remove contaminating bacteria, and preferably between about 0.22 and about 3 microns. A particularly preferred drug metabolizing system can be created by adding between about 0.25 grams and about one micromole per milliliter (mm/ml) of nicotinamide adenine dinucleotide, oxidized form (NADH).

Other techniques can be used to provide the desired metabolizing capability to the bioassays. It has been demonstrated, for example, that target cells can be cocultivated with primary cell populations capable of drug metabolism. Marguardt, H. and Heidelberger, C., *Cancer Res.,* 32, 721–5 (1972).

The following examples further illustrate the invention.

EXAMPLE 1

Assay for Mutation of Human Lymphoblasts by Methylnitrosourea

Crystalline form methylnitrosourea (MNU) was dessicated and preweighed into aliquots. The quantitative electronic absorption spectra of one of these preweighed aliquots dissolved in phosphate buffered saline (PBS), pH7.2, was determined and found to remain stable for more than 60 minutes when kept cold. Fresh solutions were prepared 10 minutes prior to dosing by dissolving preweighed aliquots in PBS and filter-sterilizing the solutions. They were then used immediately for dosing cultures and simultaneously characterized by electronic absorbance spectra.

The line of human lymphoblasts used, which is designated MIT-2, is a clonal derivative from a starter culture of the PBLC-33 line originally isolated from a young female with mononucleosis. This cell line was grown in continuous exponential phase (doubling time, 16.8 hours) by daily dilution with RPMI 1640 medium with antibiotics) supplemented to 10% with fetal calf serum. Chromosome counts indicated that greater than 80% of the cells have 46 chromosomes.

Cell survival was measured by a soft-agar plating procedure that was originally devised for mouse myeloma cells and latter extended to human lymphoblasts. Coffino, P., Baumal, R., Laskov, R. and Scharff, M. D., "Cloning of Mouse Myeloma Cells and Detection of Rare Variants," *J. Cell Physoil.*, 79, 429–440 (1972); Sato, K. Slesinski, R. S. and Littlefield, J. W., "Chemical Mutagenesis at the Phosphoribosyl Transferase Locus in Cultured Human Lymphoblasts," *Proc. Natl. Acad. Sci. (U.S.)*, 69, 1244–1248 (1972). For plating efficiencies, confluent feeder layers were used of a fibroblast strain derived from a patient afflicted with the Lesch-Nyhan syndrome. Cells of Lesch-Nyhan patients are refractory to the toxic effects of 6-thioguanine (6TG) because they lack hypoxanthine guanine phosphoribosyl transferase (HGPRT) activity. The feeder layer was overlayed with a separation layer formed from 2.5 ml of RPMI 1640 medium containing 0.25% agarose (M.C.I. Biomedical), which was allowed to gel at room temperature (10 min). The cells were suspended in 2.5 ml of 0.25% agarose-RPMI 1640 layered over the separator layer; this layer was then allowed to gel before the plates were incubated at 37° in humidified air containing 5% $CO_2$. On the following day, 1.0 ml of RPMI 1640 medium was placed on each plate, and another 1.0 ml was added 6 days later. Although microscopic colonies could be counted on day 7, 14 days were allowed in order to permit an increase in colony size to about 0.4 mm because this permitted the use of an automatic colony counter (Artek Systems). Cell counts in suspension were accomplished by counting samples on an electronic particle counter (Coulter Electronics).

Cultures of MIT-2 line in exponential growth were treated with various concentrations of MNU and resuspended 24 hours after the addition of chemical in fresh medium. By quantitatively diluting or concentrating the cell populations in each flask following the daily cell counts, they were maintained in the range of $2-8 \times 10^5$ cells/ml.

When cumulative cell growth demonstrated that sixteen or more generations of cell division has occurred after treatment with MNU, samples from the cultures were withdrawn for determination of the mutant fraction. These samples were plated in the presence and absence of 10 μg/ml of 6-thioguanine (6TG). On the day of plating, an estimated 1000 live cells/plate were used for cell survival determination, and $5 \times 10^5$ live cells/plate were used for mutant determination. An upper limit of $5 \times 10^5$ total cells/plate applies to normal growth of 6TG-resistant ($6TG^R$) clones.

Figure 2:
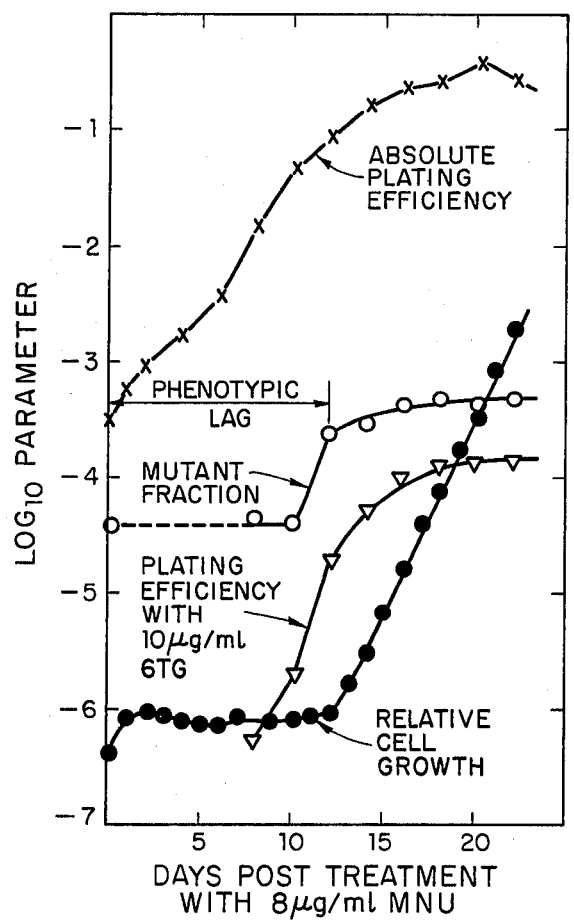
FIG. 2 is a plot illustrating phenotypic lag in the expression of 6-thioguanine (6TG) resistance in a culture of human lymphoblasts (MIT-2) initially treated with 8 μg/ml of methylnitrosourea (MNU)

A study of the dynamics of cell growth in a culture initially treated with 8 μg of MNU/ml was made and the results are plotted in FIG. 2. Cells (total particles) were counted daily and the plating efficiency of the particles in the presence or absence of 10 μg of 6TG/ml was determined by plating every other day, beginning on day 2. A dependent, fourth parameter, i.e., mutant fraction, is equal to the ratio of plating efficiency in 6TG presence of the plating efficiency in 6TG absence. Before the culture's apparent cessation of growth, as degree of association between $HGPRT^-$ (HGPRT negative by enzyme assay) and $6TG^R$ phenotype in this system. The following clones were isolated: a series of methylnitronitroso guanidine (MNNG)-induced $6TG^R$ clones; another series of spontaneous appearing $6TG^R$ clones; and, the 6TG-sensitive ($6TG^S$) (wild-type) clones. The HGPRT activities and concentration-dependent resistances to 6TG were determined for these clones. The 4 $6TG^R$ clones, 2 spontaneous and 2 MNNG-induced, were randomly selected from the available clones and studied for their behavior during each of the following steps in the mutation assay: indicated by particle counting, the population increased by about 2.25 times despite treatment with a highly toxic dose of MNU. However, the absolute plating efficiency curve distinguished live cells from dead ones, as a particle counter could not, and it revealed a rapidly dividing sub-population of survivors over the entire course of the experiment. Since the number of total cells that can be plated has an upper limit of about $5 \times 10^5$ total cells per 60-mm dish, the existence of $6TG^R$ cells could not be detected until a minimum plating efficiency of $5 \times 10^{-7}$ (clones/particle) was reached. $6TG^R$ cells were found by the eighth day after treatment, and their plating efficiency eventually reached a stable maximum of $1.3 \times 10^{-4}$ of observed clones per plated particle.

The absolute plating efficiency in the absence of 6TG (clones observed/particle plated) reached a stable maximum of about 0.28. In turn, the derived parameter, mutant fraction, eventually reached a stable maximum at $(1.3 \times 10^{-4}/0.28)$ or $4.6 \times 10^{-4}$ $6TG^R$ clones per total plated clones ($6TG^R$ and $6TG^S$). On days 8 and 10, the observed mutant fraction was the same $(4 \times 10^{-5})$ as that observed in the population prior to MNU treatment. It then increased on days 12 and 14 to a stable maximum for days 16, 18, 20, and 22. The values on days 8 and 10 were significantly different form those on days 16-22, indicating that new phenotypic variance with $6TG^R$ appeared between days 8 and 16. This same behavior was observed in five other MNU-treated cultures performed in which the final mutant fraction was significantly greater than the untreated controls. The only observed variation concerns the exact time of full phenotypic expression, which seemed to vary from 12 to 16 days.

Figure 3:
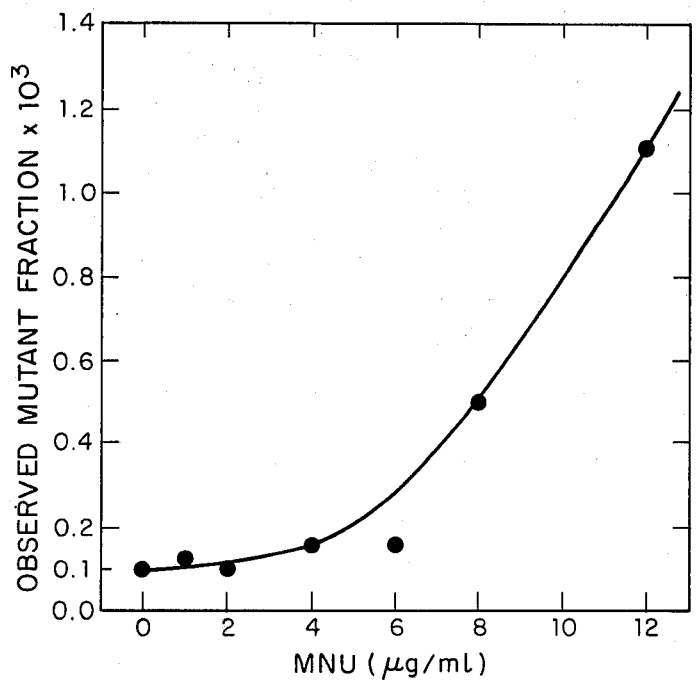
FIG. 3 is a plot illustrating the dose-related mutagenecity of MNU to a human lymphoblast line (MIT-2)

The observed mutant fraction is plotted as a function of MNU concentration of FIG. 3. Values are the mean of at least four different platings after the observed mutant fraction reached a miximum, as shown in FIG. 3. The observed background mutant fraction of 4 ($\pm 2$) $\times 10^{-5}$ was higher than desirable and tended to obscure the response, if any, in the dose range of 0.6 μg/ml of MNU. Despite this, a monotonic increase in mutant fraction seemed to occur in this range and was followed by a much faster rate of increase beginning between 6 and 8 μg/ml of MNU and lasting through 12 μg/ml.

EXAMPLE 2

Reconstruction Experiments

A series of reconstruction experiments was performed to evaluate the selective advantage or disadvantage of $6TG^R$ cells in relation to wild-type cells during the several steps of the assay protocal. In these experiments, several spontaneous and induced $6TG^R$ mutants were examined in terms of their behavior on the conditions of the mutation assay. The aim was to discover the 1. dose-dependent sensitivity to MNU among these clones was compared to that of the wild-type population, in order to determine whether treatment with chemical agents might exert a selective pressure.

2. the growth of each clone at several extremely low starting concentrations (1, 10, and 100 live cells/ml in suspension) and in the presence of heat-killed wild-type cells (6 × 10⁵ dead cells/ml) was measured immediately after treatment, in order to detect any difference between the behaviors of the mutants and the wild-type cells under conditions similar to the culture state.

3. The possible selective effects of growth under normal condititions of cell density and medium renewal were studied as follows: four 6TG$^R$ clones were paired with four subcultures of stock 6TG$^S$ culture; each of the eight cultures was then grown in three sets of 100-ml screw-top bottles, each containing 25 ml of medium; one set of bottles (set A) was diluted to 2 × 10⁵ cells/ml every day. Set B was diluted every other day, and set C was diluted every third day. In this way, different maximum cell densities for each set were achieved so that a study of the differential effects of high cell concentrations (>10⁶ cell/ml). This study lasted approximately seven weeks, or about 80 generations in the most rapidly growing cultures (Set A).

4. The same four 6TG$^R$ clones were tested for plating efficiencies in medium containing 10μg of 6TG/ml, either in the presence of absence of 5 × 10⁵ 6TG$^S$ cells/plate, in order to detect any effect of wild-type cells on the mutant number during the actual cloning process. This experiment was performed with varying concentrations of mutant cells to establish per mutant cells plated) within the range of mutant cell concentrations encountered in the assays.

The dose dependent on MNU toxicity to 4 6TG$^S$ and 4 6TG$^R$ clones, chosen at random, was as follows. 1 6TG$^R$ clone did show a high survival fraction at a relatively high concentration of MNU. However, the average behavior of the two groups was virtually identical. The fact that the clonal populations varied in sensitivity to higher MNU concentrations may reasonably be ascribed to the accumulation of "MNU-resistance" cells that arose after the cloning process some 50 generations earlier.

In the growth experiments, growth was measured by counting the clone/forming units during the daily plating of samples. Data obtained was plotted. The curves showed that all four clones grew with a doubling time of approximately 18 hours, which was close to the 16.8-hour doubling time of stock cultures. When low concentration (50 cells/ml) of 6TG$^R$ mutant cells were combined with approximately equal number of 7TG$^S$ cells and allowed to grow in the presence of heat-killed cells for 14 days, no significant change in the mutant fraction (initially 0.47) was observed.

In the experiment to study the possible selective effects, all four HGPRT$^-$ clones demonstrated the same growth behavior as their paried HGPRT$^+$ populations when the diluations occurred daily or every other day. However, when cells reached concentrations in excess of about 10⁶ cells/ml, as they did in Set C, the HGPRT$^+$ populations seemed to have a growth advantage over HGPRT$^=$ populations. It was clear that the most rapid overall growth for these stationary cultures was obtained by the schedule of most frequent medium removal.

In the experiments for plating efficiency, 2 HGPRT$^-$ clones exhibited no difference in plating efficiency, but one showed a significant decrease in plating efficiency in the presence of HGPRT$^+$ cells. However, a linear relationship for all 4 clones was obtained between cells plated and clones observed, i.e., nonmutants did not suppress mutants in the range of cloning densities normally encountered. A variation in absolute cloning efficiency was also noted among the clones that were found to be characteristic for each clonal subline was isolated.

EXAMPLE 3

Assay for Mutagenesis of Human Lymphoblast Line For Chemical Mutagens

The procedures of Example 1 were used to study the mutagenic effects of five known mutagens. These were the alkylating agents ethyl methane sulphonate (EMS), methylnitronitrosoguanidine (MNNG), methylnitrosourea (MNU), the pyrimidine analogue, bromodeoxyuridine (BUdR), and the half-mustard substituted acidine, ICR-191. The cultures were treated with approximately equimutagenic concentrations of these mutagenic agents as follows.

Suspension cultures (200 ml) of the diploid human lymphoblast line, MIT-2, were treated with the mutagens while they were in the exponential growth phase at a cell concentration of 4 × 10⁵ cells per ml in RPMI 1640 media supplemented with 10% fetal calf serum. Twenty-four hours later, cells were resuspended in fresh medium and maintained at 2 × 10⁵ cells per ml by dilution or concentration daily in fresh medium for the duration of all experiments. Cloning efficiency in the presence or absence of 10 μg per ml 6-thioguanine was determined every other day, using the agarose/feeder layer technique. Specific data regarding treatments, survival (cloning efficiency at 24 hours) and period of delay in cell multiplication can be summarized as follows:

| AGENT | CONC. (μM) | TREATMENT DURATION (HRS.) | PERCENT SURVIVING | EST. INITIAL GROWTH DELAY (DAYS) | INDUCED MUTANT FRACTION × 10⁴ |
|---|---|---|---|---|---|
| EMS | 840 | 24 | 0.12 | 0 | 6.9 |
| MNU | 50 | 24 | 0.10 | 0 | 4.8 |
| MNNG | .225 | 24 | 0.06 | 2–3 | 2.5 |
| BUdR | 50 | 24 | 9 | 0–1 | 4.2 |
| ICR-191 | 1.25 | 24 | 18 | 3–4 | 5.6 |

Control mutant fractions fell within the range of 0.05 to 0.40 × 10⁻⁴.

Figure 4:
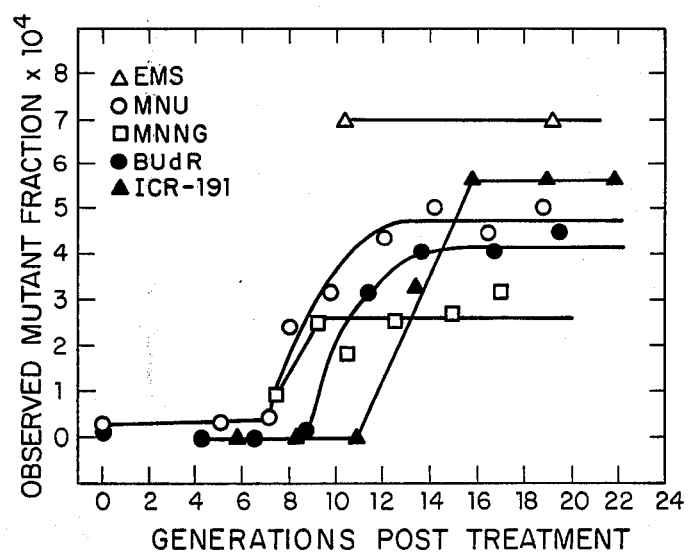
FIG. 4 is a plot illustrating phenotypic lag in the expression of 6-thioguanine (6TG) resistance in a culture of human lymphoblasts (MIT-2) following treatment with five chemical mutagens.

The growth behavior of each treated culture was defined by both electronic particle counts and by cloning efficiency determination. Thus, a determination of cellular multiplicity relative to the time of treatment for all experiments could be determined and thus, the average number of cell generations could be calculated by assuming reasonable homogeneity among the growing cells. FIG. 4 presents the mutant fraction observed for all five mutagens tested, as a function of generations after treatment. The number of divisions required for full phenotypic expression varies from a low of 9 for MNNG and EMS to a high of 16 for ICR-191. Once these mutant fractions reached a maximum, they remained constant within limits of sensitivity of the assay.

If the data of FIG. 4 were expressed in terms of elapsed time, large differences in phenotypic lag time would seem to result with treatment with different chemicals. These differences, however, seem partially attributable to the length of the period post-treatment, before cell division recommences, which varies significantly among the compounds studied.

EXAMPLE 4

Concentration-Dependent Mutation by Methylnitronitrosoguanidine

The procedures of Example 1 were used, except that methylnitronitrosoguanidine (MNNG), purchased in crystalline form from K and K Laboratories, was substituted for the methylnitrosourea.

The dose dependence of MNNG was found to be a simple, log-linear relationship up to an MNNG concentration of about 90 ng/ml. A plateau of presumably resistant cells then occurred until MNNG concentrations became greater than 150 ng/ml, at which point the surviving fractions continued to decline.

Figure 5:
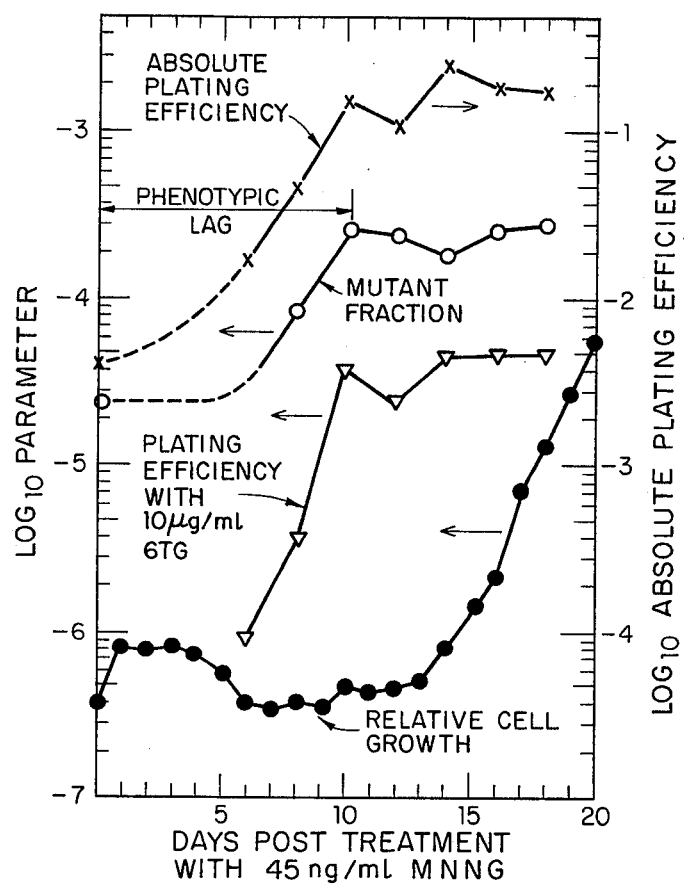
FIG. 5 is a plot illustrating phenotypic lag in the expression of 6TG resistance in a culture of human lymphoblasts (MIT-2) initially treated with 45 ng/ml of methylnitronitrosoguanidine (MNNG)

FIG. 5 presents data relevant to the phenotypic lag for MNNG-induced mutagenesis. Culture growth (particle/ml), the cloning efficiency in the presence or absence of 6TG, and the derived parameter, mutant fraction, are all illustrated for a concentration of MNNG of 45 ng/ml which was the highest level studied. The monotonic increase in absolute plating efficiency indicated that a small fraction of live cells was continually multiplying despite the apparent stoppage in cell growth, as indicated by particle counting. The total number of particles that can be placed on a 60/mm dish without inhibiting the growth of $6TG^R$ cells has an upper limit ($>5 \times 10^5$ cells per plate), and absoluting plating efficiencies are on the order of 0.25. Thus, $6TG^R$ cells must constitute more than $1/(0.25)$ ($2 \times 10^6$) of the population before they can be detected by quadruplicate plating in 6TG. Plating efficiencies in the presence or absence of 6TG eventually reached stable maximum. The derived parameter, mutant fraction rose above background on the eighth day but did not achieve a stable maximum until approximately twelve days after MNNG treatment.

Figure 6:
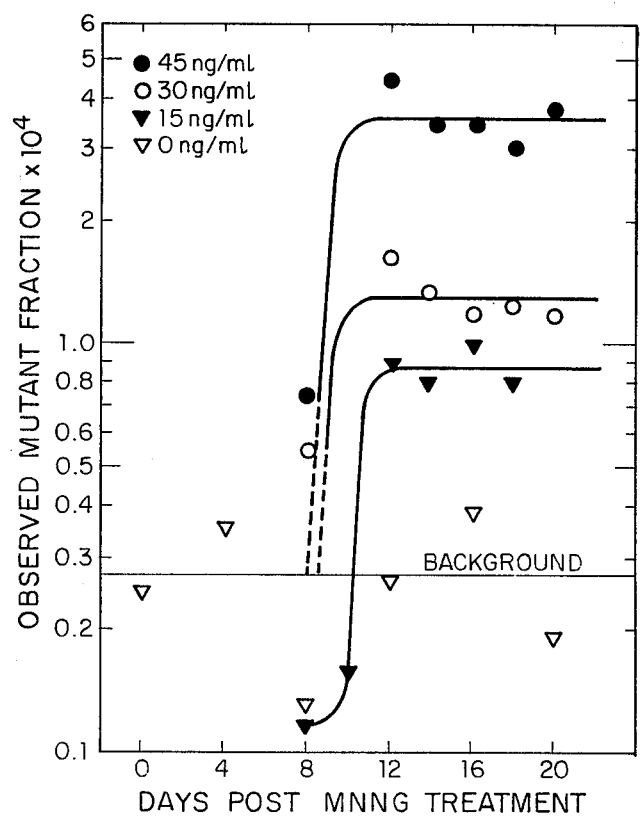
FIG. 6 is a plot illustrating phenotypic lag in the expression of 6TG resistance in a culture of human lymphoblasts (MIT-2) after treatment with varying doses of MNNG.

FIG. 6 illustrates how the observed mutant fraction of the control and MNNG-treated cultures changed as a function of time after MNNG treatment. A maximum stable mutant fraction was reached by the twelfth day for all dose levels of MNNG. Mutant fractions were significantly greater than background for all of the MNNG concentrations tested. These results did not show any significant differences between doses regarding the expression period. Small differences in expression time would not have been noticeable, however, because of the large expected variances in determining small mutant fractions, such as those observed on days 6 and 8.

Figure 7:
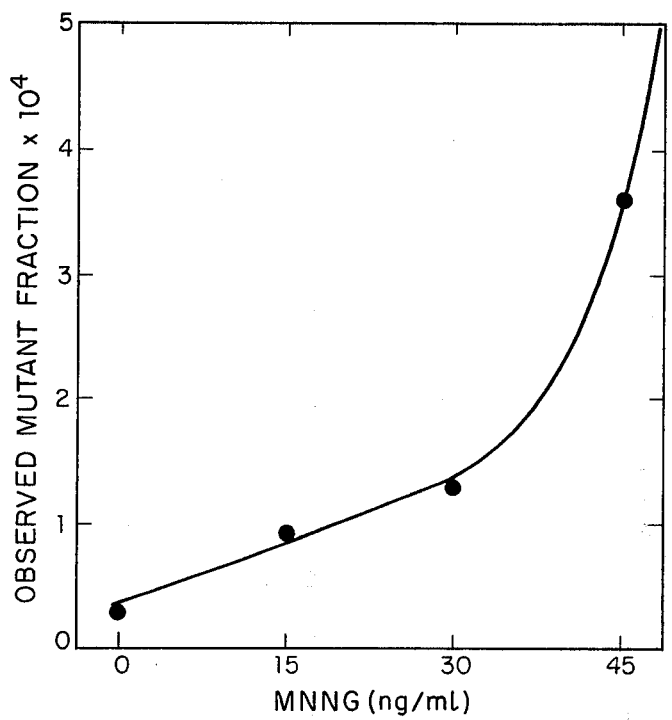
FIG. 7 is a plot illustrating dose-related mutagenicity of MNNG to human lymphoblasts (MIT-2)

Using the means of all determinations that defined the stable maximum of mutant fraction, a dose-response relationship was constructed and is illustrated in FIG. 7. As expected for a fast-acting chemical and single-hit kinetics, the induced mutant fraction rises as a linear function of MNNG concentration up to 30 $\mu$g/ml. The mutant fraction increases more steeply at the higher concentrations tested. The concentration range used in this mutagenicity study is well within the log-linear toxicity response and corresponds to surviving fractions of 5% and higher.

EXAMPLE 5

Sensitivity of Wild-Type and Mutant Clones to 6TG and HGPRT Activity of Mutant Clones HGPRT activity and plating efficiencies as a function of 6TG concentration for clones sensitive ($6TG^S$) or resistant ($6TG^R$) to 10 $\mu$g/ml of 6TG were determined.

Plating efficiencies were determined following the procedure of Example 1.

HGPRT activity was determined using a modification of a published technique. Long, C., Chan, T., Lauytska, V., Kusano, T. and Green, G., "Absence of Demonstrable Linkage of Human Genes for Enzymes of the Purine and Pyrimidine Salvage Pathways in Human-mouse Somatic Cell Hybrids," *Biochem. Genetics*, 9, 283–297 (1973). The following reagents were combined in a total volume of 0.10 ml: 1mM phosphoribosylpyrophosphate (PRPP) (Sigma); 6.25 mM $MgCl_2$; 15 $\mu$M [$^3$H]hypoxanthine (5 Ci/mmole) (New England Nuclear); 139 mM NaCl; 1.0 mM EDTA: and 70 mM Tris buffer, pH7.4, containing 0.02 ml of 1:10 dilution ($5 \times 10^6$ cells/ml of 102 mM NaK phosphate) of the supernatant fraction of cell sonicate (centrifuged at 40,000 $\times$ g for 60 min at 4° and sonicated with 2 $\times$ 15 sec bursts on a Branson Sonifer, power setting 3. Standard incubations were performed at 37° for 30 min.

The reaction was quenched by addition of 0.025 ml of 50 mM EDTA at 0°. DE-81 2.5-cm disks (DEAE cellulose; Whatman) were spotted with 0.025 ml of the quenched reaction mixture and allowed to dry at 25°. Disks were rinsed at 25° first with 40 ml of 1 mM ammonium formate and then with 20 ml of ethanol in a standard filter-holding chimney (Millipore). Disks were dried for 10 min at 60° in scintillation vials, to which 15 ml of Aquasol (New England Nuclear) were added after the vials had cooled. The vials were then counted on a Packard 2002 scintillation counter. With this system, the overall efficiency of counting phosphorylated purines bound to DE-81 filters was $4.10 \pm 0.03\%$ (S.E., $n = 7$).

At a cell concentration of $5 \times 10^6$ cells/ml in the sonicate, the minimum concentrations of PRPP, $MgCl_2$, and hypoxanthine necessary to maintain maximum velocity for 60 min were found to be 0.50 mM, 4 mM, and 10 uM, respectively. Product formation occurred linearly with time over 60 min, with a phosphoribosylation velocity of $6.4 \pm 0.4$ mmoles of hypoxanthine/min. The reaction kinetics were first order with respect to cell equivalents of $0.25$–$4.0 \times 10^4$ cells/assay; a standard assay uses $3 \times 10^4$ cell equivalents.

The results are presented in the following table:

| | RELATIVE SURVIVING FRACTION | | |
|---|---|---|---|
| | -Wild Type (HGPRT⊕) Clones- | | |
| Clene | HGPRT | $\mu$g/ml 6TG: | | |
| Number | Activity | 0.10 | 1.0 | 5.0 |
| MIT-2 | 100% | $9.4 \times 10^{-3}$ | $3.3 \times 10^{-4}$ | |
| W8 | n.t. | .66 | $2.3 \times 10^{-5}$ | $<1.3 \times 10^{-6}$ |
| W11 | n.t. | .64 | $2.9 \times 10^{-5}$ | $2.6 \times 10^{-5}$ |
| | -Mutant Type (HGPRT⊖) Clones- | | |
| Clone | HGPRT | $\mu$g/ml 6TG: | | |
| Number | Activity | 5 | 10 | 20 |
| D3 | <.2% | | .71 | .73 |

-continued

| | RELATIVE SURVIVING FRACTION | | | |
|---|---|---|---|---|
| P1 | <.2% | 1.12 | .75 | .86 |
| P2 | <.2% | 1.73 | 1.21 | .94 |
| P6 | <.2% | 1.03 | .97 | .67 |
| P7 | <.2% | .80 | .60 | .54 |
| P9 | <.2% | .86 | .45 | .22 |
| P10 | <.2% | .81 | .41 | .30 |
| P11 | <.2% | 1.00 | .55 | .24 |
| P15 | n.t. | .87 | .58 | .27 |
| P18 | <.2% | .55 | .62 | .45 |
| B2 | n.t. | .94 | 1.00 | .71 |
| B4 | n.t. | 1.6 | 1.5 | 1.1 |
| B6 | n.t. | 1.1 | .82 | .76 |
| B7 | n.t. | 1.2 | .66 | .57 |
| B8 | n.t. | 1.0 | .93 | .80 |
| B9 | n.t. | 1.1 | 1.2 | .68 |
| B13 | n.t. | .86 | 1.0 | .45 |
| B15 | n.t. | .71 | .87 | .37 |
| B17 | n.t. | 1.1 | 1.4 | 1.6 |
| B20 | n.t. | .90 | .83 | .51 |

Of about 40 6TG$^R$ clones examined (some not shown), only one had any detectable HGPRT activity. The assay was sensitive to $\geq 0.2\%$ of normal activity. Since the determination of HGPRT and 6TG resistance took place after a minimum of 40 generations' growth in the absence of selective conditions, the data in the Table demonstrate the phenotypic stability of 6TG resistance as well as the association between this resistance and the loss of HGPRT activity.

EXAMPLE 6

Preparation of Drug Metabolizing System

A male Sprague-Dawley rat weighing about 130 grams was killed by decapitation and its liver was removed and washed in ice-cold homogenization medium consisting of 1.5% KCl, 3 mM Mg Cl$_2$, 62.5 mM phosphate buffer, pH 7. The liver was then placed in fresh homogenization medium (25% wet weight/total volume), minced well, and then homogenized in a Dounce apparatus, using 5 strokes with a loose-fitting pestle. The homogenate was spun at 9,000 g for 30 minutes in a refrigerated centrifuge (4° C.). The supernatant (PMS) was carefully decanted and placed on ice.

Prior to use, the PMS was filtered serially through the following Millipore filters (25 mm size):

0.80 $\mu$ with cotton prefilter
0.45 $\mu$
0.30 $\mu$
0.22 $\mu$ (sterilized).

The first three filters were prewetted with distilled water because it is extremely difficult to push PMS through a dry filter. This procedure prepared approximately 25 ml of sterile PMS.

EXAMPLE 7

Effect of Filtration

The effect of filtration of aryl hydrocarbon hydroxylase (AHH) activity was studied. A 2% PMS preparation was prepared as specified in Example 6. A control was used which was prepared by this procedure except that the PMS was not filtered.

The assay procedure for AHH activity was essentially the same as that described by Nebert et al. in the literature. Nebert, D. W. and Gielen, J. W., *Fed. Proc.*, 31, 1315–1325 (1972). The incubation medium was 7 mM MgCl$_2$, 80 mM NADP+, 2 mM glucose-6-phosphate, 79 benzopyrene and contained 0.167 mg/ml bovine serum albumin in a total volume of 3.0 ml. 33 mM phosphate buffer was used to maintain pH at the observed optimum of 7.0.

All cofactor concentrations are derived from studies with ad libitum fed male Sprague-Dawley rats ranging in body weight of 150–200 gms. Thus, Mg++ requirements were found to be somewhat higher than Nebert and Gielen reported, for instance.

The specific procedure consisted of preincubating all components (2.9 ml) except benzo($\alpha$)pyrene for 5 min in a 37° shaker bath. Benzo($\alpha$)pyrene was added in 100 $\mu$l of DMSO and incubation continued for 15 minutes before quenching with 3 ml acetone. This mixture was then extracted by 10 minutes shaking with 9 ml hexane at 37°. Recovery experiments with pure 3-hydroxybenzopyrene showed >90% recovery by this procedure. 1 ml of the hexane phase was placed in 5 ml 1 N NaOH, mixed, and allowed to stand for 4 min at room temperature. Following a second mixing, the aqueous solution was removed and its fluorescence determined in a Turner Fluorometer, Model 111. The extractions served to separate benzo($\alpha$)pyrene from the 3-hydroxy product. A bandpass filter was used to provide excitation in the region of 396 nm and a barrier filter was used in measuring all fluorescence above 475 nm.

The results were expressed in relative fluorescence units. Relative fluorescence units corresponds to a 2.5 $\mu$M solution of 3-hydroxy benzo($\alpha$)pyrene in the original 3 ml incubation mixture.

Figure 8:
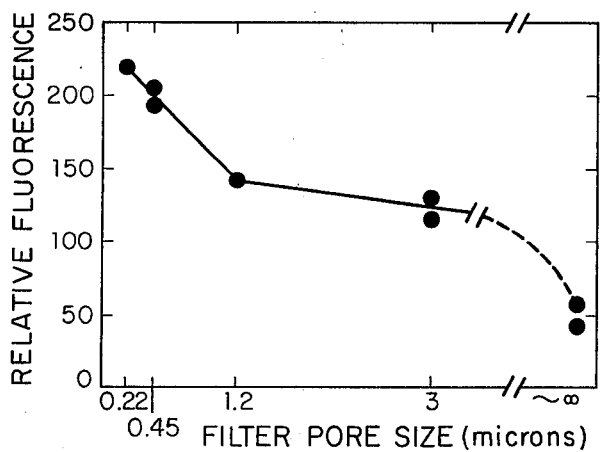
FIG. 8 is a plot illustrating the effect of filter pore size on aryl hydrocarbon hydroxylase (AHH) activity in a drug-metabolizing system prepared from rat liver post-mitochondrial supernatant (PMS)

Data obtained are plotted in FIG. 8 which illustrates the effect of filter pore size on total AHH activity. Filtration with a 0.22 micron filter (Millipore) increased total AHH activity approximately fourfold relative to unfiltered PMS.

EXAMPLE 8

EFFECT OF NADH ADDITION

Figure 9:
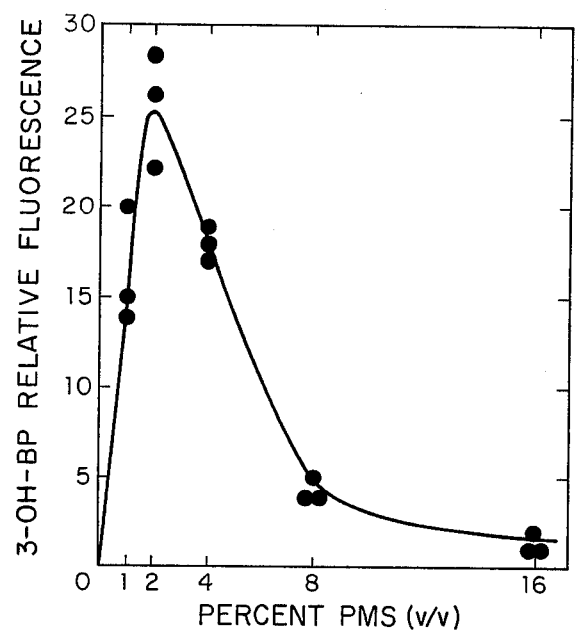
FIG. 9 is a plot of AHH activity at different concentrations of PMS.
Figure 10:
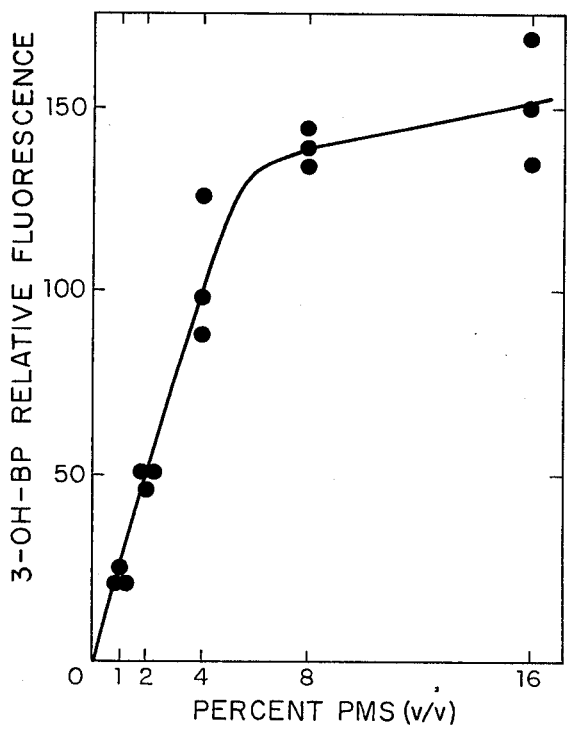
FIG. 10 is the same, except that the PMS contains NADH.

The procedure of Example 6 was used, except that 320 $\mu$M of NADH was added to the incubation mixture. The increase in AHH activity obtained is illustrated in FIGS. 9 and 10, wherein a sixfold increase in overall AHH activity for PMS containing NADH can be seen compared to a control having no NADH.

EXAMPLE 9

COMBINED EFFECT OF FILTRATION OF NADH ADDITION

Figure 11:
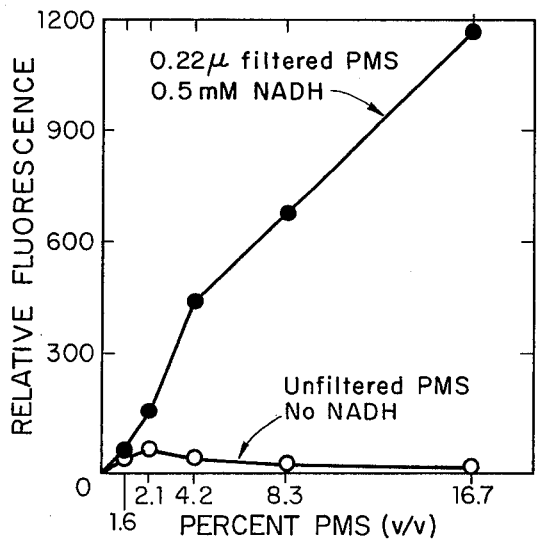
FIG. 11 is a plot of AHH activity at varying concentrations of filtered PMS which also contains NADH.

A PMS sample was prepared following the procedures of Example 6, except that 0.5 $\mu$M NADH was added to the incubation medium with methylcholanthrene-induced rats. The data obtained are plotted in FIG. 11, and it can be seen that the overall effect was nearly a 25-fold increase in total available AHH activity relative to unfiltered controls without NADH.

Those skilled in the art will recognize many equivalents to the specific embodiments of the invention described herein. Such equivalents are considered part of this invention and are intended to be encompassed by the scope of the following claims.

What is claimed is:

1. An assay for determining mutagenesis, comprising:
   a. exposing a culture of human diploid or near-diploid cells capable of continuous division in suspension culture and having one active x-chromosome which carries the gene for HGPRT to an agent to be tested for its mutagenic effects on said cells;
   b. incubating exposed cells for a number of generations sufficient to allow full expression of phenotypically-developed resistance to a purine which acts as an HGPRT substrate; and then, c. detecting the amount of mutant cells to thereby determine the degree of mutagenesis.

2. The assay of claim 1 wherein said purine is 6-thioguanine.

3. The assay of claim 1 wherein said cells comprise human diploid lymphoblasts.

4. The assay of claim 3 wherein said purine is 6-thioguanine.

5. The assay of claim 1 wherein an active, drug-metabolizing system is added to the cell cultures.

6. The assay of claim 4 wherein an active, drug-metabolizing system is added to the cell cultures.

7. The assay of claim 6 wherein said active, drug-metabolizing system comprises a post-mitochondrial supernatant of homogenized mammalian tissue in an aqueous suspension medium, said post-mitochondrial supernatant having been filtered to remove contaminating bacteria.

8. The assay of claim 7 wherein said drug-metabolizing system also contains NADH.

9. The assay for determining mutagenesis comprising:
a. exposing a culture of a human, diploid, lymphoblastoid cell line to an agent to be tested under conditions whereby at least some of the cells survive;
b. resuspending exposed cells in fresh medium;
c. incubating the resuspended, exposed cells for a sufficient number of generations to allow the expression of the substantially fully phenotypically-developed cell resistance to a purine HGPRT substrate; and,
d. determining the induced mutant fraction.

10. The assay of claim 9 wherein said purine HGPRT substrate is 6-thioguanine.

* * * * *